(12) United States Patent
Boender

(10) Patent No.: US 8,915,969 B2
(45) Date of Patent: Dec. 23, 2014

(54) HYDRAULIC PROSTHETIC JOINT

(76) Inventor: Jacob Quintus Laurens Anthony Boender, Oxford (GB)

( * ) Notice: Subject to any disclaimer, the term of this patent is extended or adjusted under 35 U.S.C. 154(b) by 95 days.

(21) Appl. No.: 12/737,834

(22) PCT Filed: Oct. 27, 2009

(86) PCT No.: PCT/GB2009/002557
§ 371 (c)(1),
(2), (4) Date: Feb. 18, 2011

(87) PCT Pub. No.: WO2010/049681
PCT Pub. Date: May 6, 2010

(65) Prior Publication Data
US 2011/0307078 A1    Dec. 15, 2011

(30) Foreign Application Priority Data

Oct. 27, 2008    (GB) .................................. 0819554.7

(51) Int. Cl.
    *A61F 2/74* (2006.01)
    *A61F 2/64* (2006.01)
    *A61F 2/60* (2006.01)
    *F16F 9/512* (2006.01)
    *A61F 2/68* (2006.01)
    *A61F 2/50* (2006.01)
    *A61F 2/76* (2006.01)

(52) U.S. Cl.
CPC . *A61F 2/68* (2013.01); *A61F 2/642* (2013.01); *A61F 2002/5007* (2013.01); *A61F 2002/5039* (2013.01); *A61F 2/605* (2013.01); *A61F 2002/741* (2013.01); *A61F 2002/5006* (2013.01); *F16F 9/512* (2013.01); *A61F 2002/745* (2013.01); *A61F 2002/5018* (2013.01); *A61F 2002/5033* (2013.01); *A61F 2002/748* (2013.01); *A61F 2002/7635* (2013.01)
USPC ............................................. 623/26; 623/44

(58) Field of Classification Search
CPC ................ A61F 2002/5007; A61F 2002/5006; A61F 2002/5039; A61F 2/64; A61F 2002/642; A61F 2002/741; A61F 2002/745; A61F 2002/748; A61F 2/68
USPC .......................... 623/26, 27, 39, 43, 44, 45, 46
See application file for complete search history.

(56) References Cited

U.S. PATENT DOCUMENTS 5,371,137 A    12/1994    Blincow et al.
5,383,939 A *    1/1995    James ............................. 623/24
(Continued)

FOREIGN PATENT DOCUMENTS

GB    779087    9/1982
GB    2282414 A    4/1995
(Continued)

*Primary Examiner* — Marcia Watkins
(74) *Attorney, Agent, or Firm* — Galvin Patent Law LLC; Brian R. Galvin

(57) ABSTRACT

The present invention relates to artificial limbs generally and to joints for the same. In particular, the present invention provides hydraulic functional units (35), generally classified as damping devices as connected between artificial limbs whereby to enable movement of artificial joints to closely correspond with natural human movement. In the provision of realistic joints, as used in prosthetic limbs, an important aspect in attempting to achieve a realistic movement is to provide a different operating characteristic to the joint when under load. Indeed, one of the more important characteristics of an artificial leg for achieving a natural-looking walking gait correspond with those of a so called stabilized knee, i.e. a knee which resists flexion when under load, that is when it is bearing at least some of the weight of the amputee. In accordance with the invention, there is provided hydraulic damper control elements for prostheses which utilize a pressure differential due to the presence a fluid flow as a direct control input for a at least one hydraulic valve (47). The valve can comprise a vortex flow arrangement (47*f*) to cause fluid flow to circulate about aperture. The valve can comprise a moveable element which abuts a resiliently mounted element which reduces the size of an aperture as the force increases.

18 Claims, 12 Drawing Sheets

(56) References Cited

U.S. PATENT DOCUMENTS

| | | | |
|---|---|---|---|
| 5,545,233 A * | 8/1996 | Fitzlaff | 623/43 |
| 5,571,205 A * | 11/1996 | James | 623/24 |
| 6,106,560 A | 8/2000 | Boender | |
| 6,113,642 A * | 9/2000 | Petrofsky et al. | 623/24 |
| 6,613,097 B1 * | 9/2003 | Cooper | 623/44 |
| 6,978,872 B2 | 12/2005 | Turner | |
| 2007/0198098 A1 * | 8/2007 | Roston et al. | 623/26 |
| 2007/0208431 A1 * | 9/2007 | Bisinger et al. | 623/39 |
| 2008/0300692 A1 | 12/2008 | Moser | |

FOREIGN PATENT DOCUMENTS

| | | |
|---|---|---|
| WO | WO2007/016408 A1 | 2/2007 |
| WO | WO2007/095993 A1 | 8/2007 |
| WO | WO2009/015473 A1 | 2/2009 |

* cited by examiner

PRIOR ART

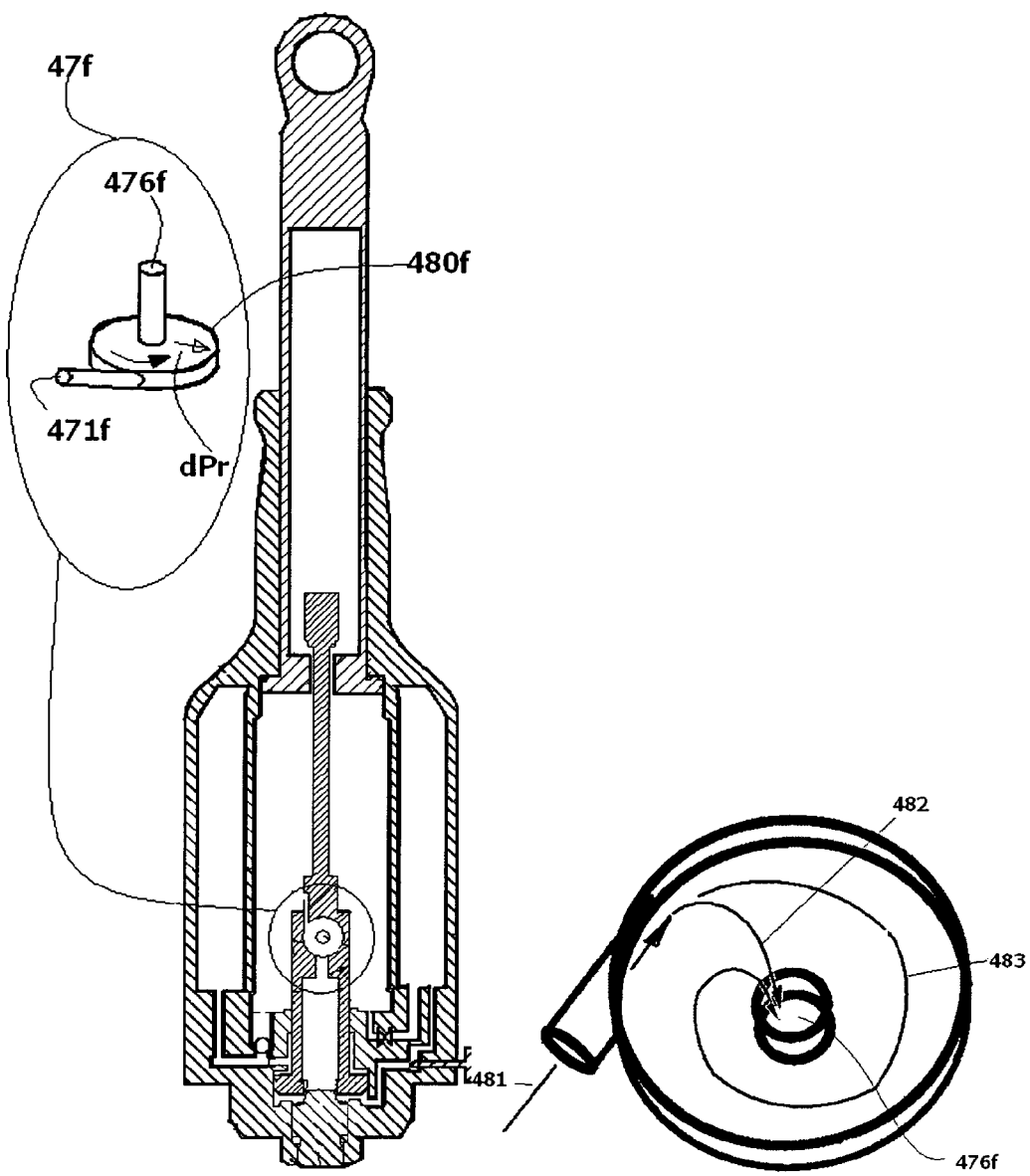
Figure 4f
Figure 4g
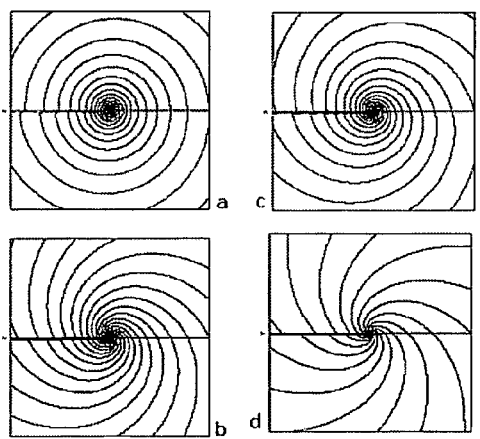
Figure 4h

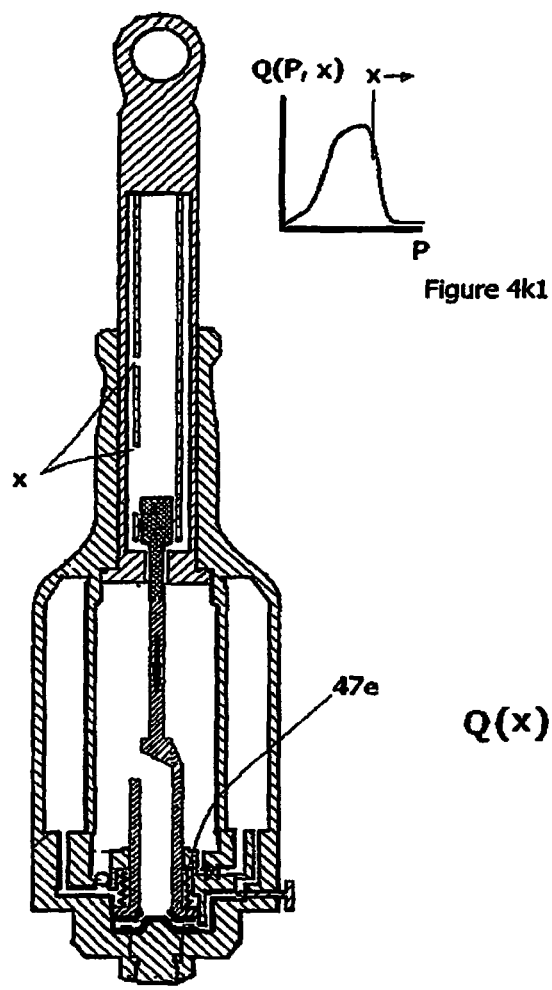
Figure 4k1
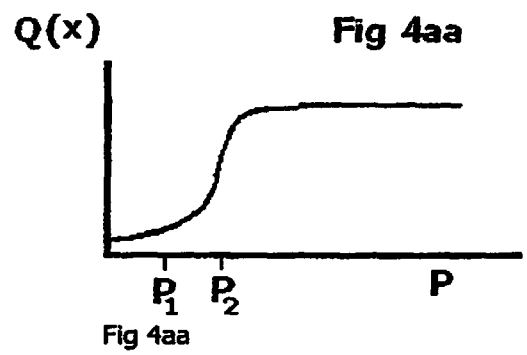
Fig 4aa
Figure 4k
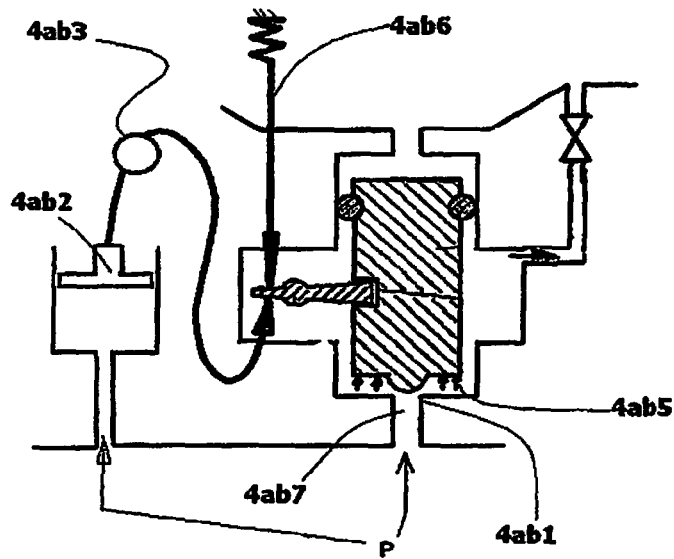
Figure 4ab  PRIOR ART
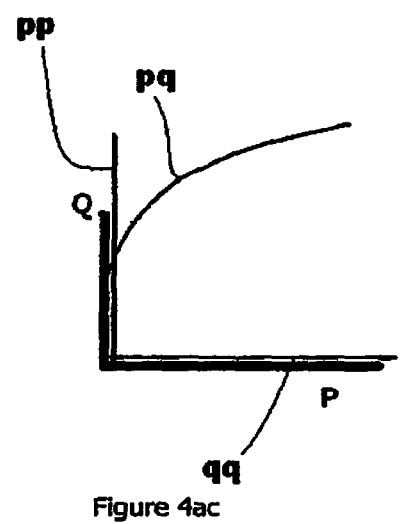
Figure 4ac

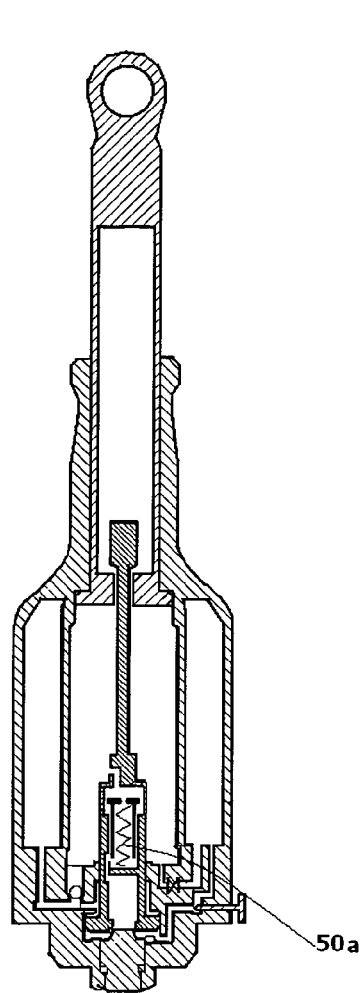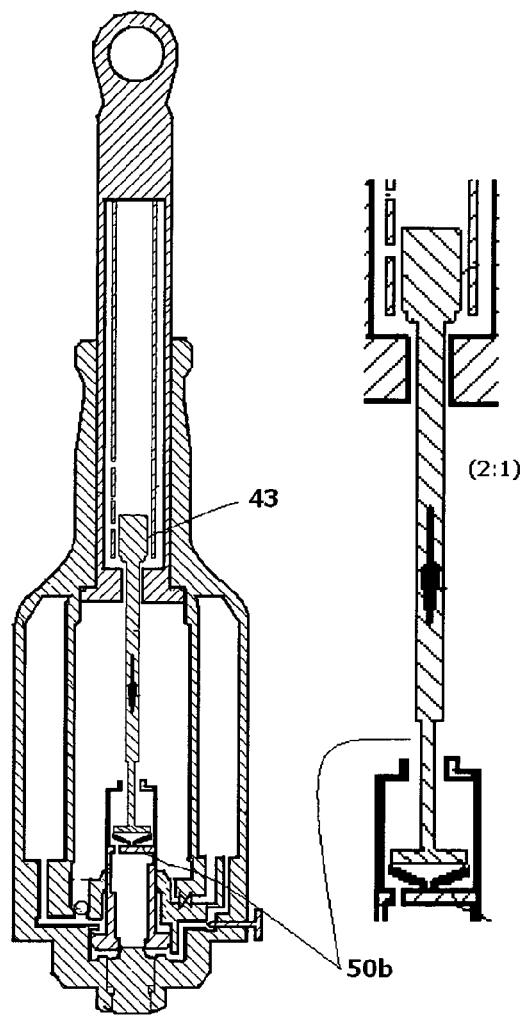
Figure 5a
Figure 5b
Figure 5b section scale 2:1
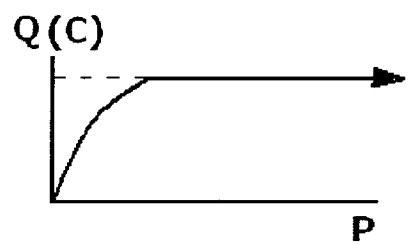
Figure 5ai

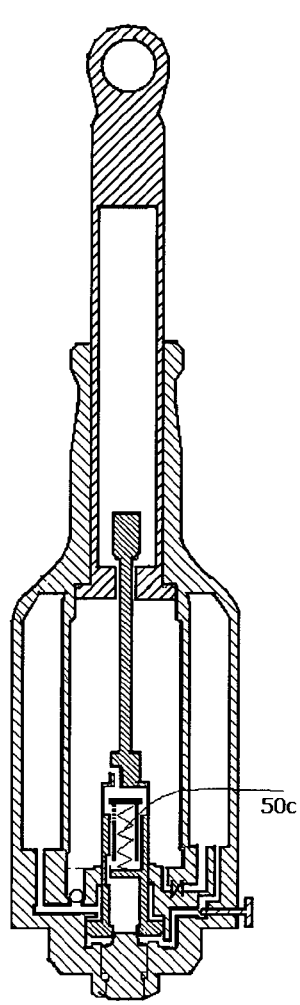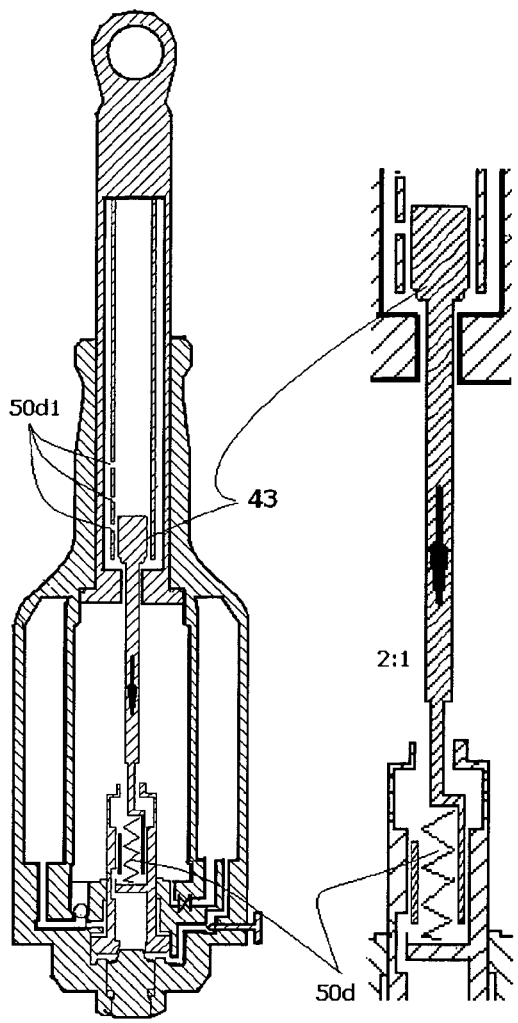
Figure 5c Figure 5d Figure 5d section scale 2:1
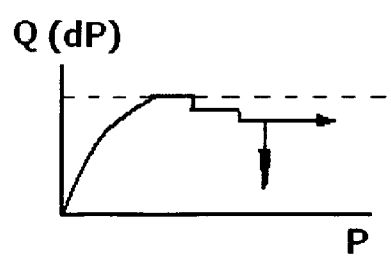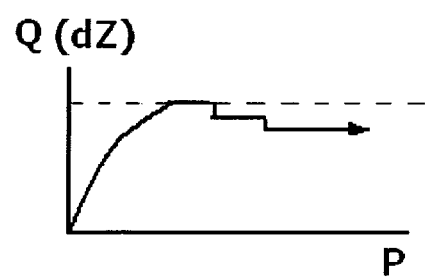
Figure 5ci Figure 5di

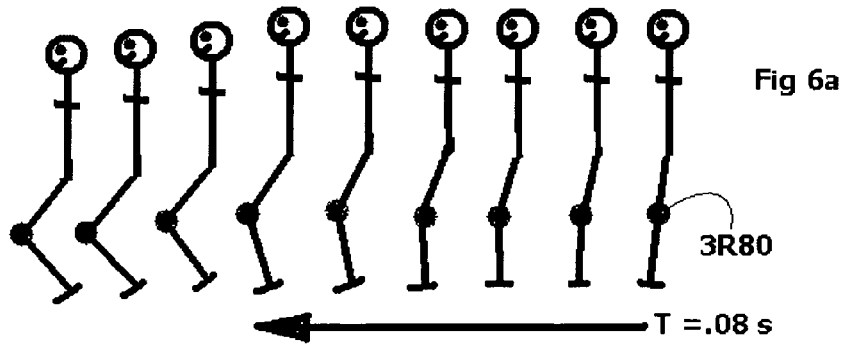
Fig 6a
3R80
T = .08 s
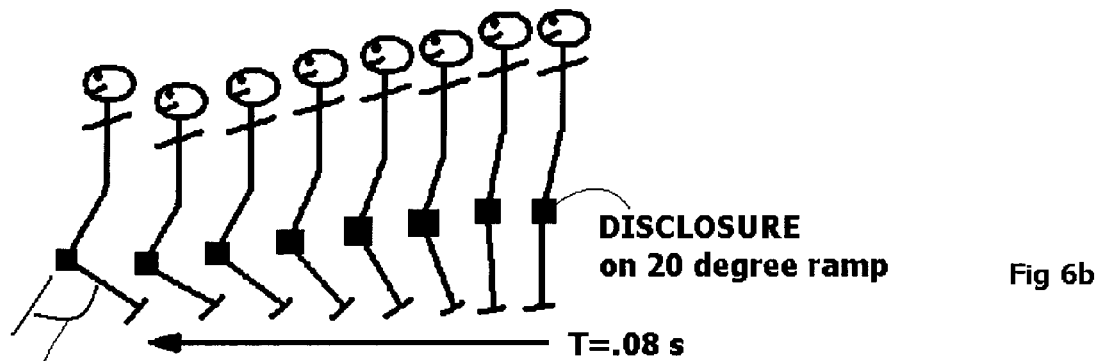
DISCLOSURE on 20 degree ramp
Fig 6b
T = .08 s
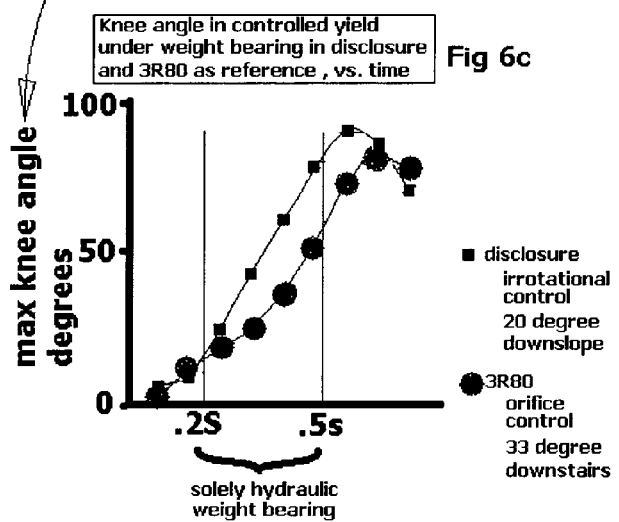
Fig 6c
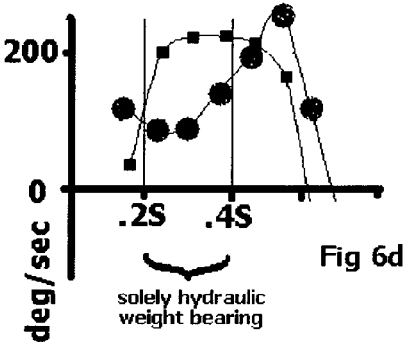
Fig 6d
Figures 6a-6d

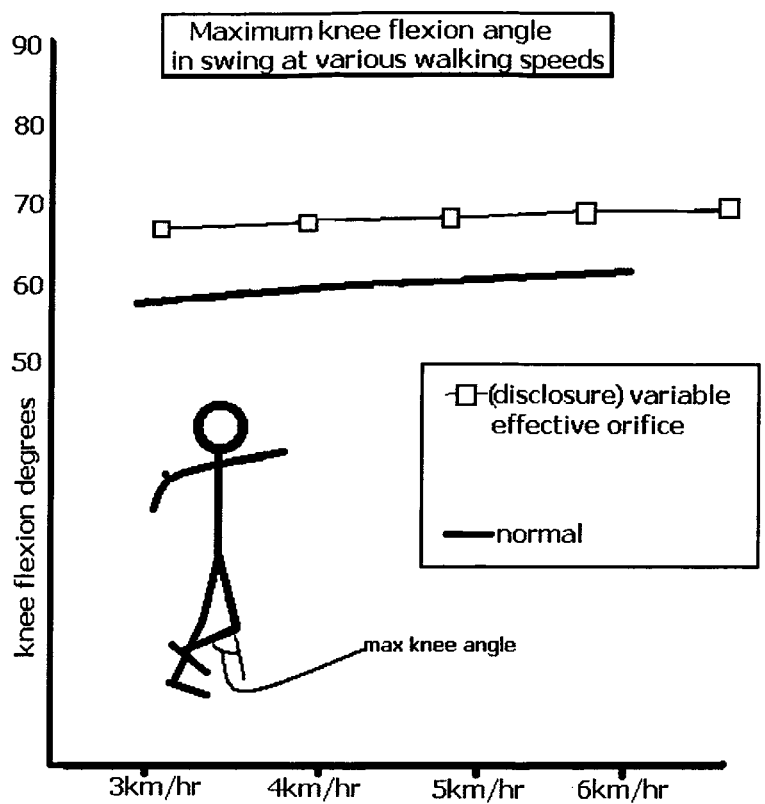
Figure 7
Figure 8
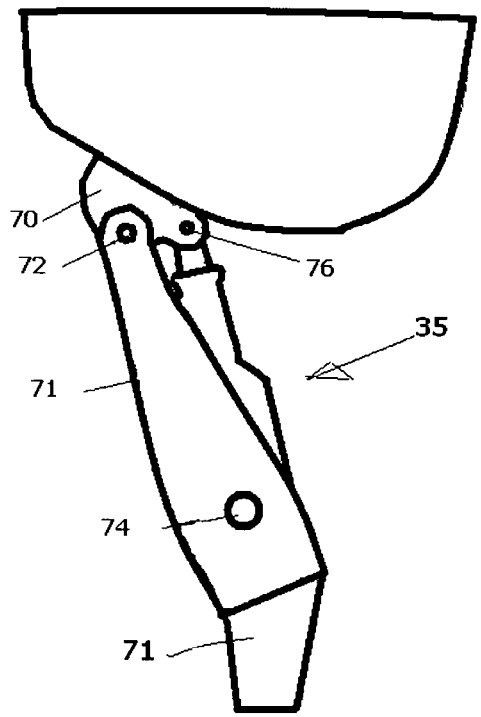

HYDRAULIC PROSTHETIC JOINT

FIELD OF THE INVENTION

The present invention relates to artificial limbs generally and to joints for the same. In particular, the present invention provides hydraulic functional units, generally classified as damping devices as connected between artificial limbs whereby to enable movement of artificial joints to closely correspond with natural human movement.

BACKGROUND

In the provision of realistic joints, as used in prosthetic limbs, an important aspect in attempting to achieve a realistic movement is to provide a different operating characteristic to the joint when under load. Indeed, one of the more important characteristics of an artificial leg for achieving a natural-looking walking gait correspond with those of a so called stabilised knee, i.e. a knee which resists flexion when under load, that is when it is bearing at least some of the weight of the amputee. It can be said that the test is somewhat subjective if one were to view an amputee with an artificial leg, but mere observation is one of the best tests; a strange gait is generally immediately apparent; this can cause unwelcome stares to amputees, who when fitted with a pair of long trousers would otherwise not be noticed when in a crowd. Reference is made to literature associated with the Advanced Prosthetics course by J. Boender at Strathclyde University, which provides a detailed review of artificial knee joints.

Early prosthetic limb systems; dating from the 1950's were provided with friction brake devices. For example, in GB779087, when utilized in a knee joint application, there was a provided a shin and knee joint mechanism which included a drum fixed to the shin, with one or more bands connected to the thigh and embracing the drum so that the bands gripped the drum to lock the knee when the leg was bearing weight, actuating means associated with the shin and thigh operated to release the lock just before the foot left the ground in walking, with a connection between the shin and thigh permitting relative axial movement between the shin and thigh. In this device, however, an axial load on the limb produced a small rotation of the radius arm or arms causing the brake band or brake shoe to grip the drum and to resist knee flexion. Indeed, the resistance would frequently become so great such that the knee became automatically locked once sufficient load had been applied. Later devices were combined with a pneumatic piston and cylinder assembly which applied lower degrees of resistance to flexion and/or extension of the knee to control the motion of the shin during the swing phase.

In recent years, however, such friction-based systems—which required regular servicing and adjustment have been replaced by hydraulic dampers with external control, which provide resistance to flexion during a stance phase as well as a swing phase of operation by means of a piston and cylinder, assembly. Hydraulic artificial knees provide stability to the prosthesis when the patient's weight is borne on the prosthesis, and collapse must be prevented. To prevent collapse of a free artificial knee joint the joint must receive appropriate information to inform it of its required mode of function. The hydraulic knee joint operates by utilising a volume of incompressible fluid to the knee joint, whereby to provide mechanical stability.

One example of such an arrangement is the hydraulic "S-N-S" knee control system manufactured by Mauch Laboratories, Inc. In some situations, however, this system required an amputee to make a knee-extending movement before flexion could be initiated. Additional problems arose through external wear and through the fact that they require actuation, which is, of course dependent upon movement being regular. As is known, when walking, one will vary one's gait to go down stairs, to cross steps, to avoid obstructions and the like. In some cases mechanical switching of the valve will not be effected properly. U.S. Pat. No. 5,376,137 to Blatchford is an example of a weight activated knee joint with hydraulic amplification of weight application triggered pivotal movement, whilst U.S. Pat. No. 6,106,560 to Ultimate Knee teaches of a weight activated knee joint with mechanical amplification of weight application triggered pivotal movement.

Whilst recent hydraulic devices are believed to be much improved they are complex and costly to manufacture; they are manufactured to high tolerances. If mechanical external valve control is provided, then there will be problems as discussed above. Alternatively, electronic control and flow control valves can be provided—that are expensive to purchase and maintain—which enable amputees to walk with a pre-determined gait yet will not necessarily be reactive to uneven surfaces.

To assist in the understanding of the problems addressed by the present invention, reference shall now be made to standard testing techniques, as employed to assess the fitness of an amputee to walk with or without assistance. FIG. 1 is a graph that represents the maximum knee flexion angle in swing at various walking speeds for three known devices of prosthetic knee joints, (Source: "What are the benefits of the C-Leg?" (J. Kastner, R. Immervoll, H. Kristen & P. Wagner)). The graph shows a clear change of at least 10° in angular variation of knee flexion movement as an increase in walking speed for the computer controlled device yet a change of 20° over a speed change of 2 km/h for a known mechanically controlled device. The plot of knee flexion for a normal gait, i.e. for a person with the full use of their own limbs is shown for comparative purposes. It can be seen that the variation in knee flexion angle is more or less absent, for a control person, with full use of their own legs, despite an increase in speed to approximately double that of the initial speed. In simple terms, to the casual observer, the person wearing such artificial limbs would be seen to have an ungainly gait due to a delay in knee extension needed to prepare the limb for weight acceptance. In another study "User-adaptive control of a magneto-rheological prosthetic knee" (H. Herr and A. Wilkenfeld) which appeared in Industrial Robot: An International Journal Volume 30, Number 1, 2003, 42-55, where a computer controlled prosthesis—a Rheo Knee—was tested. A horizontal response was produced but the study was limited to below 5 km/hr limit, which is less than normal walking speeds.

Certain prostheses provide joints that use a weight activated safety mechanism which is energized by forces present in weight bearing, a weight bearing on the artificial limb, that can be detected and be made effective in implementing a change in resistance to limb pivoting. Such a movement can be the compression of one of the members that form a mechanical chain from the amputation stump to the ground, and which can be detected by strain gauges, by small amounts of telescopic deformations, or limited ranges of pivotal movements such as the knee or ankle and can typically be detected as relative displacements of two suitably chosen points. The pivotal movements can be amplified mechanically (including hydraulically) or electronically and/or can be made to be more sensitive to forces transmitted through a heel of an artificial foot as opposed to those input through a fore part of a foot.

Problems arising from the use of weight activated knee joint control mechanisms include the fact that the residual weight taken by the artificial limb on toe off can be inhibitive to the release of the weight-activated mechanism. Typically an apparatus or means is supplied to cause a threshold value of weight required to activate the knee stability. This threshold is easily overcome by force entry through the heel and is not easily overcome by force entry through the toe. Nevertheless, this threshold takes away from the ease of activation on heel strike, which subtracts from the total ease of use of the artificial limb, and low grades of attention will be needed at all times.

The same threshold also makes it difficult to find instant effortless stability of the knee, when extension after mid swing is incomplete the respective foot is susceptible of hitting the ground too early. This is particularly true when traversing rough pathways. Typically the weight-activation class of knee joints do not provide security against collapse in such conditions or in the event of accidental use.

One difficulty to be overcome by users of prosthetic lower limbs is that it is counter intuitive to place one's body weight onto the device to secure the same body weight against sudden collapse. This is not a problem in certain types of knee which default to a weight acceptance mode; the knee stability is deactivated by a mechanism that detects hyperextension of the knee joint, which typically goes together with a load on a fore-foot part of the prosthesis, but which can also be provided by voluntary hip femoral stump hip extension. Again there is a small movement that can inform the knee design of a required change of status, and also here various similar signal amplification means can be employed, i.e. mechanical, electronic, hydraulic.

Whereas the weight activated mechanisms have their weight application input parameter present throughout an activation period, the hyperextension that deactivates the knee stability mode is removed as soon as the joint commences its permitted free flexion to support the required free knee flexion for swing, as required in the use of a free knee, which requires the joint to have a memory, for a period as long as the knee is in free flexion mode, being a preceding condition of hyperextension. This period corresponds to the first half of the pendulum swing movement of the shank of the prosthesis relative to the thigh member. Additionally, the memory mode must be deactivated on knee extension in order to return the knee joint to its default state, where it must be ready to take an amputee's weight.

FIG. 2 details a switching function of the Mauch SNS prosthesis, wherein the memory function is determined by a mechanical arrangement (as opposed to an electronic timer arrangement, for example). Specifically, the memory comprises an eccentric toggle (H1), that resumes a gravitational neutral position unless prevented by an open state of a valve member (H3), which is energized by hydraulic pressure (H4) caused by a flex movement of the free knee. It is notable that this linkage is not instantaneous; release of the memory function takes a time frame independent of the time it takes to reapply weight on the prosthesis. In the event of an inadvertent early reapplication of weight on the prosthesis, the toggle would likely not be in a position to allow closure of the valve, which could be painful and perhaps cause an amputee to fall over following knee collapse in such circumstances. In effect, the memory of this prior teaching is continued for a longer period than desired whereby to cause at the very least a non-natural gait, with an increased likelihood of a fall occurring due to the time required for a change in state being far greater than desirable.

In the case of hip prostheses, it would be advantageous if the hip were furnished with a hydraulic apparatus which would immediately take a load on heel strike, and allow the patient to sink into the fluid of the hydraulic apparatus with such a speed that the socket remains substantially more in a position of a neutral pelvis.

OBJECT TO THE INVENTION

The present invention seeks to overcome or ameliorate at least some of the disadvantages described above. It is a further object of the invention to utilise the fluid properties of the working fluids and the architectures of the ducts and passages to enable purely mechanical system. Notwithstanding this, it is a further object of the invention to permit alternative embodiments such as for example electronic, electro fluidic or electromechanical means.

It is a still further object of the invention to provide a simple to use prosthesis which is not vulnerable to ingress of water and dirt and can be both simply and easily cleaned. Another object of the invention to provide a leg prosthesis that enables a more immediate release of a memory function, but remain sensitive to a required completion of the knee flexion movement in the first half of the swing phase, when required as is the case across uneven terrain.

STATEMENT OF INVENTION

In accordance with the present invention, there is provided a prosthesis in accordance with the features of claim 1. The present invention thus utilizes a pressure differential due to the presence a fluid flow as a direct control input for a at least one hydraulic valve.

The valve can comprise a vortex flow arrangement to cause fluid flow to circulate about an aperture, wherein at a critical speed of flow the vortex defines a void which diminishes the size of the effective aperture.

The valve can comprise a moveable element which abuts a resiliently mounted element which reduces the size of an aperture as the force increases and acts against the resiliently mounted element or can comprise a piston operable within a bore having a closed end and equipped with a valve, the variable volume being defined between the piston and the closed end of the bore.

The hydraulic actuator can comprise one of a rotating vane in a suitable housing assembly, a cog pump, a moveable end portion of a bellow body, in which embodiments either part can be said first means, or in which said first means is a membrane or a free piston sealing a fluid space, which said membrane or free piston converts an external hydraulic fluid pressure on the outer membrane or free piston face into a force through the body of the membrane, which said body of the membrane or free piston converts the force into the said first pressure.

The limb can be a leg, with the first artificial limb component being an upper leg element and the second artificial limb component being a lower leg or a hip element, the joint pivotally coupling said first and second limb being a knee or hip joint. The limb can be an arm with the first artificial limb component being an upper arm element and the second artificial component being a lower arm limb or shoulder element, the joint pivotally coupling said first and second limb being an elbow or shoulder joint.

The prostheses in accordance with the present invention can comprise one of or both an artificial skeletal limb or a brace for hip, limb or ankle. Conveniently, the valve is adjustable to provide variable conditional control to the motion of said joint by permitting changes to its angular status. The fluid can be selected from one of a combination of the following fluids; a hydrocarbon based fluid, a silicone based fluid or rheomagnetic fluid.

Thus, in one aspect of the present invention, upon a return to a natural weight accepting state of the knee joint there is no delay to a further state of movement of the joint, for example, upon the occurrence of lifting off the weight of a body upon a prosthesis, the lower part is free to swing in a controlled fashion i.e. a state permitting free knee flexion), this by drawing on the energizing and informing potential of the existing reverse pressure differentials present during the extension phase in the second half of the swing phase. Due to the relative high levels of energizing power available during knee extension and the distinct and logical onset of its availability, its use is an inherent advance in the logical control of an artificial hydraulic knee. Notwithstanding this, if further delay is required, then additional control systems could be employed, to act in an ancillary fashion. A further enhancement and alternative is the making available to a user an adjustable time delay for the memory to turn to a default sate.

In another aspect, the use of flow pressure differentials conditions a normally closed valve to remain open; in different modes of use of a joint this serves to provide data to the effective memory of the system, to keep a normally closed valve open, and optionally use these pressure differentials as a means to energize the memory. Further, the use of the reverse flow pressure conditions as present, for example in an extension of a knee joint, can provide data to the effective memory of the system, to return to a quiescent state, to lose any memory upon extension, and optionally use these reverse pressure differentials as a means to effect a change of memory content is a second part of this aspect of the invention.

BRIEF DESCRIPTION OF THE DRAWINGS

Reference shall now be made to the drawings as shown in the accompanying drawing sheets, wherein:

FIGS. 4a-k, 4aa-4ac, and 4k1 detail valves and operational response graphs in accordance with aspects of the invention;

FIGS. 5a-5e show different hydraulic dampers in accordance with the invention with certain corresponding response graphs;

FIG. 6a-d show graphs and tracking photos of embodiment of the present invention and a prior system;

FIG. 7 is a graph that represents the maximum knee flexion angle in swing at various walking speeds for a knee joint of the invention; and FIGS. 8 a & b show flow and schematic diagrams in accordance with the present invention.

LEXICON

The following terms have specific meanings and it is intended that reference shall be made to this lexicon in event of any doubt:

Brace: a support device to maintain a relative position of a limb with respect to the trunk or another limb; part of an external frame work arrange about and intended to support limbs;

Hydraulic fluid; a substantially incompressible fluid operable in hydraulic lines, hydraulic rams and hydraulic systems;

Hydraulic damper: a hydraulic device comprising at least a first variable volume of hydraulic fluid, wherein the volume of hydraulic fluid retained within the hydraulic actuator is proportional to an amount of actuation associated with a joint to which the hydraulic damper is coupled;

Prosthesis: an artificial part such as an artificial limb; an artificial or mechanical aid such as a brace;

Prosthetic joint: an artificial joint associated with the repair or replacement of a skeletal joint; the term includes external orthopaedic joints;

Orthopaedic joint: a skeletal joint; a joint of the limbs; a joint such as the hips;

Valve: a device operable to regulate or control the flow of a fluid in a passageway, such as a pipe or duct, between two volumes; a device operable to regulate or control the flow of a fluid, but not necessarily preventing flow of said fluid;

DETAILED DESCRIPTION OF THE PREFERRED EMBODIMENTS

There will now be described, by way of example only, the best mode contemplated by the inventor for carrying out the present invention. In the following description, numerous specific details are set out in order to provide a complete understanding to the present invention. It will be apparent to those skilled in the art, that the present invention may be put into practice with variations of the specific.

Figure 1:
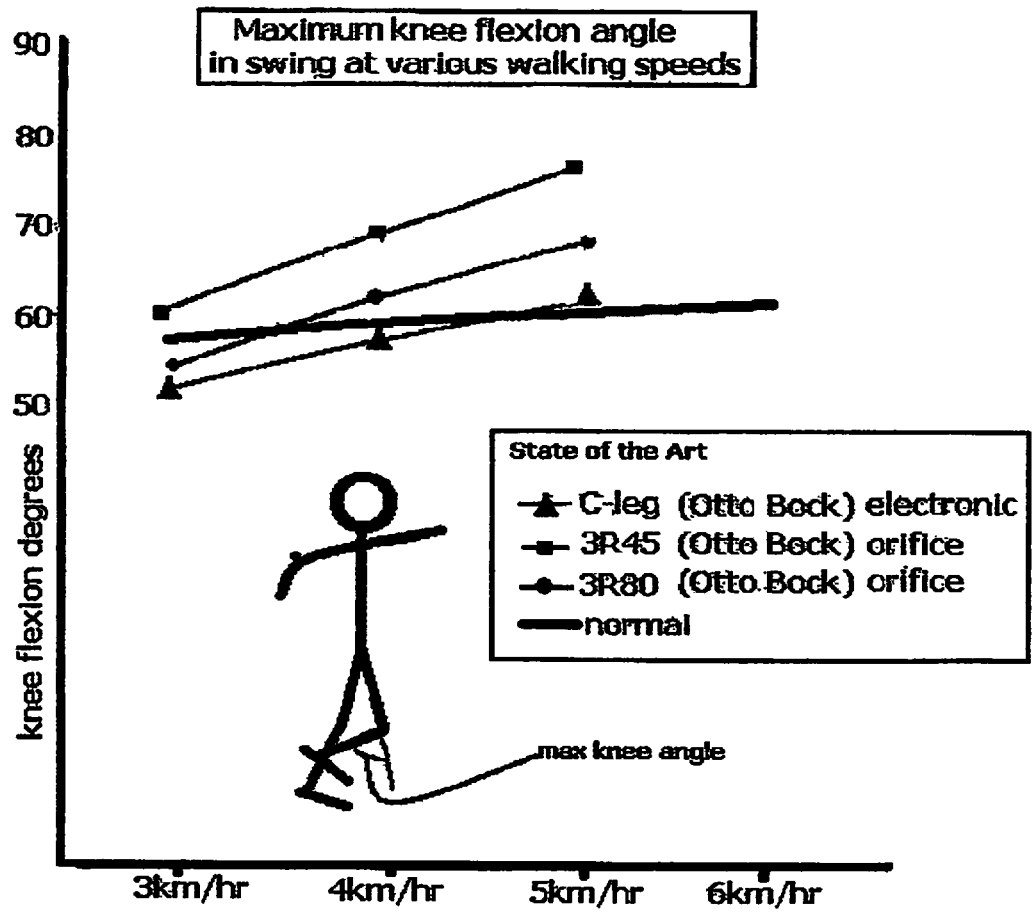
FIG. 1 is a graph that represents the maximum knee flexion angle in swing at various walking speeds for prior art prosthetic knee joints.
Figure 2:
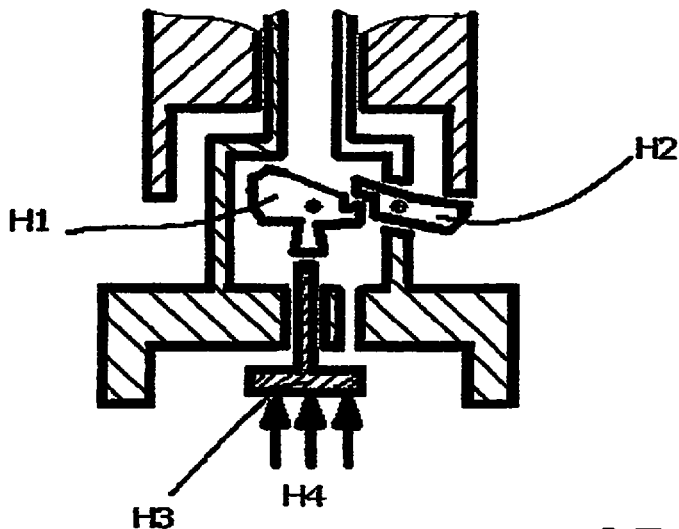
FIG. 2 details a known prosthesis hydraulic switch.
Figure 3:
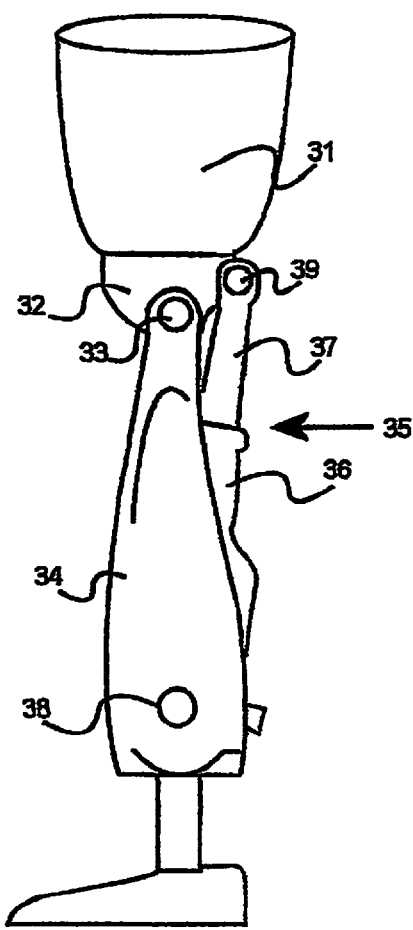
FIG. 3 shows a leg prosthesis with a hydraulic damper.

FIG. 3 shows a simple artificial leg arrangement 30, wherein an upper leg member 31 terminates with a stump element 32, which is pivotally connected to a lower leg member 34 by means of joint 33. A main body 36 of a hydraulic damper 35, having a main body 36, is connected with the lower leg 34 at coupling point 38, which coupling point 38 allows relative movement therebetween. A member 37 of the hydraulic damper 35 is connected to the stump element 32 at coupling point 39 and is similarly arranged for movement, in this case, relative to the stump element 32. Whilst the following description describes the hydraulic damper in relation to a lower leg prosthesis, it is to be understood that the hydraulic damper can be utilised in relation to other prosthetic orthopaedic skeletal joints, for example a hip to an upper leg joint, an upper arm to a shoulder, etc.

One general problem associated with mechanical joints is that the response of the joint controller is dependent upon a load applied and not necessarily to a kinematic requirement that commands a movement pattern independent of load as possible. This means that a correct and safely maintained response is required in each of the two alternating operating states of a prosthetic; namely, a low reactive torque state, such as typically in a swing phase, and a state of high reactive torque under weight bearing. An inappropriate torque level typically means a severe disruption of gait.

Figure 4:
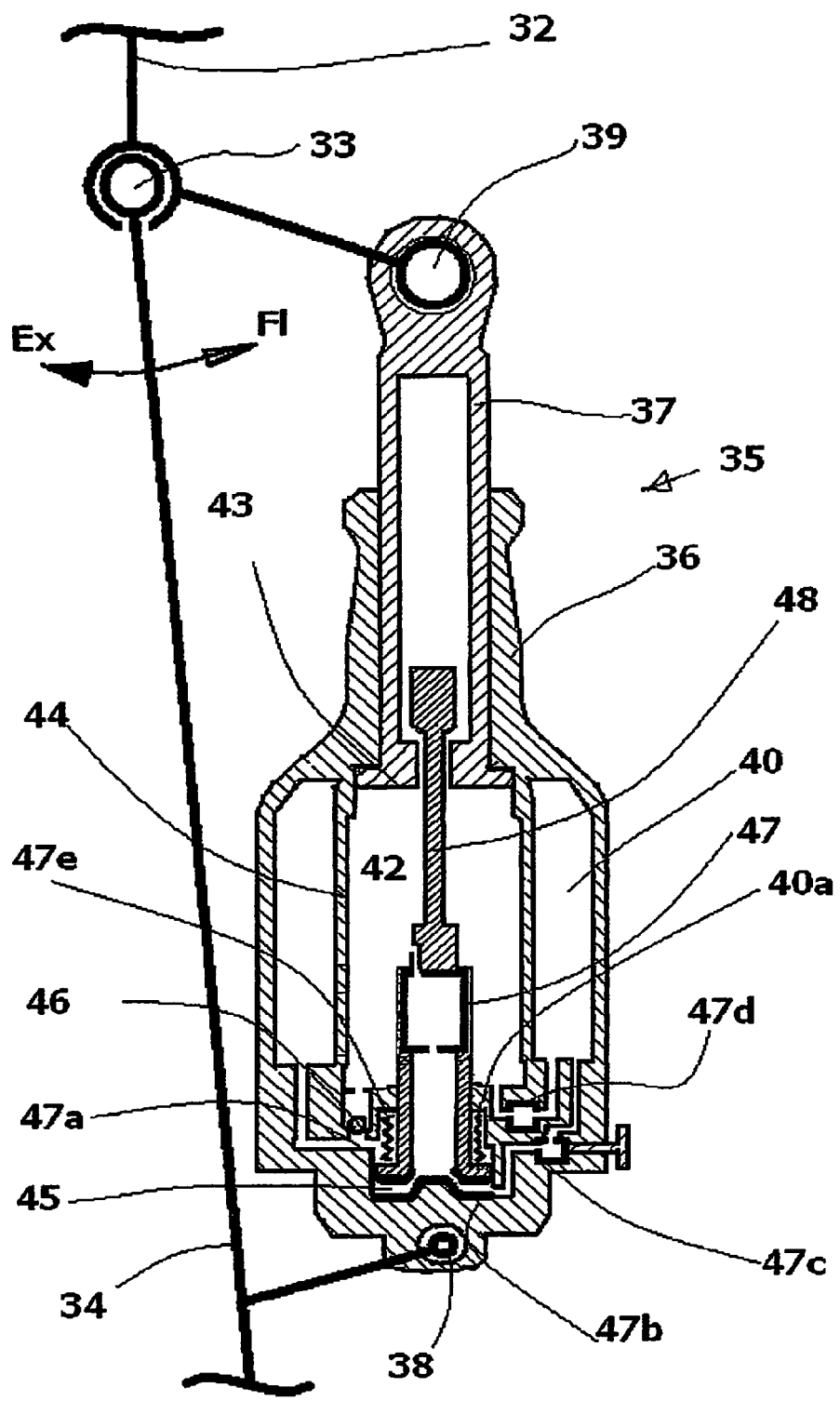
FIG. 4 is a cross-section through a generic device in accordance with the invention.

Referring now to FIG. 4, there is shown a simplified view of the invention. Hydraulic damper unit 35 comprises a hydraulic arm element 37 which is coupled to an artificial leg part 32 by connection 39 at an end opposite to that of a main body 36 and by connection 38 at an end opposite to that of hydraulic arm element 37 with artificial leg part 34. Hydraulic arm element 37 comprises a piston 43 which moves relative to bore 44 to define a variable volume chamber 42. Hydraulic fluid from the variable volume chamber 42 is operable to pass to valve 47 into an accumulator 40 via fluid path 45. Indeed, in some embodiments, the valve assembly could comprise part of the piston assembly. In use, as the piston approaches valve 47, fluid is caused to go through the valve; the rate of flow of fluid is controlled by the valve; since the valve reduces the flow rate under high pressure, then the movement of the damper is conditioned to be gradual. However, upon withdrawal of the piston, away from the valve, then one way valve 46 can allow free and unhampered return flow of hydraulic fluid from the accumulator to the variable volume chamber 42. Element indicated 48 serves to raise the seat 47a of valve 47 from a valve seat 47b. Flowpath 47c leads from valve 47 towards accumulator 40. As will be appreciated, the space 40a (which is at the same pressure as in the accumulator) between the valve base and the base of the bore will be filled as the pressure within the valve area urges the valve 47 towards the piston and further descent of the piston 43 will maintain fluid flow.

Use of the hydraulic damper fitted to a prosthesis shall now be discussed, with the limb element 32 comprising an upper leg element and limb element 34 comprising a lower leg limb and the joint 33 being the knee. The knee will operate over an angular range, typically, of 120°. In ambulatory mode, the lower leg will extend forwardly and flex rearwardly. Accordingly in flexion mode (indicated by arrow denoted Fl) the piston 43 will approach the valve in compression, reducing the volume of the variable volume chamber 42, causing fluid flow through the valve 47, conditional upon the valve faces 47a and 47b being separated. The valve faces can only be separated if prior to the separation the widened top portion of element 48 has been raised by the reduced width or neck section of the piston by a degree of overextension of the knee joint that effectively causes withdrawal of piston 37 from cylinder 36. On immediate flexion effort, and after this brief event, fluid flow is still possible through valve seat 47a, 47b and, which in turn, immediately builds up a pressure between 47a and 47b, due to a flow resistance arising through gate 47c. As long as flexion continues, fluid flow through area 47c will continue, maintaining the pressure that is conditioning valve seat 47a to remain separate from valve seat 47b. The pressure in the vicinity of valve seat 47c will maintain this state because the opposing pressure in volume 40a is not greater than the reference pressure in accumulator 40. If the hyperextension does not happen and the piston is pressed straightaway, then auxiliary valve 47d will operate in default and shall allow limited movement, allowing fluid transfer from the variable volume chamber through to the accumulator albeit at a reduced rate; the pressure in volume 42 ensuring maintenance of fluid pressure on body 48 causing valve 47 to remain closed.

In contrast, in extension mode, with movement in direction corresponding to arrow Ex, the pressure in valve 47 is lower than in the accumulator, which will mean the gap 40a is increased to a maximum as the accumulator fluid acts in the area of this gap. Simultaneously, the one way valve 46 will open allowing the accumulator fluid to enter into the variable volume chamber 42, causing extension of the hydraulic arm 37 as the piston is caused to withdraw from the valve 47.

The force of the hydraulic pressure induced by the flow within the variable volume chamber is transmitted (in certain embodiments, for example see example valve per FIG. 4d) by connecting rod 48 to the valve, whereby operation of the valve is directly controlled by such hydraulic pressure. In such arrangements, an outlet aperture of the valve reduces in size; In the examples hydraulic pressure acting on the valve causes an aperture to be physically occluded, as will be discussed in further detail to the specific valve mechanisms below, whereby to reduce the flow of fluid from the variable volume chamber, with the result that movement of the piston within the bore is reduced and so any movement is effectively "damped".

It is to be understood that when valve 47a-47b is almost—but not fully—closed, spring 47e will provide a force to close the said valve 47a-47b. However, a flow through the valve is present and builds a pressure level in front of gate 47c, which said pressure as a function of the flow conditions the 47a to be lifted against spring tension 47e. When the driving pressure of variable volume chamber 42 increases a little, the valve portion 47a lifts a bit more and a variable aperture between valve seats 47a and 47b increases in size, reducing the pressure drop across it. The lift in valve portion 47a is also associated with an increase in force 47e and more pressure is required to cause further valve lift. Advantageously the valve can be made to have the fluid flow condition the dynamic state of the aperture. FIG. (4aa) shows a response rate typical for this arrangement.

This is in contrast to, for example, the disclosure in U.S. Pat. No. 6,106,560 to Ultimate Knee, wherein a flow through a valve 4ab1 supports an open state default of that valve, and under no circumstance could there be brought into effect a corresponding state of dynamic balance between valve position and rate of flow. The effective piston action 4ab2 via linkage system 4ab3 pushes valve 4ab1 to close, yet same pressure P pushes valve 4ab1 to open acting on surface 4ab5. Spring 4ab6 defaults valve 4ab1 to an open state. When valve 4ab1 is closed, P can only act on section of valve seat 4ab7, which is too small to cause valve 4ab1 to open. This is a bi-stable configuration only, and not a flow conditioned valve.

Figure 4A:
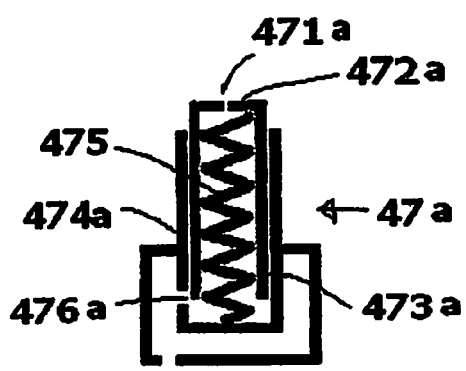

FIG. 4ab shows that essential elements of a damper in accordance with the general principles of U.S. Pat. No. 6,106,560. A pressure P acts on a valve body causing a lift of the valve body, but the same pressure also acts on the main damper piston of the knee that produces a reaction force that feeds back onto a swiveling part to cause a valve closure force that acts in parallel and conjunction with a resilient element to default the valve into an open state. Only when the valve is closed and no fluid passes through aperture the main damper piston can maintain valve closure due to the fact that pressure P acts on a smaller effective face of the said valve body.

The teaching of U.S. Pat. No. 6,106,560 thus provides a bistable valve and cannot, therefore, be advantageously conditioned by any degree of fluid flow. The accompanying graph per FIG. 4ac further clarifies the response of this valve arrangement in response to a flow through the valve. When there is no flow Q=0 for all pressures, (qq), and when the valve is open Q can be anything as a P-Q function of the downstream valve, and the curve (pq) in the graph reflects that. The true response of the valve being open in the presence of pressure P is the near vertical flow function (pp).

The advantage of the flow conditioned performance of the disclosure is found in the possibility to have a valve that permits a swing movement in the knee, but also allows a gradual closure of the valve on termination of the initial knee flexion movement, so that the valve does not abruptly closes and ads the finishing touch on termination of knee flexion, which said finishing touch provides comfort and quality in proprioceptive feedback to the user.

FIG. 4k discloses further flow conditioning of said valve, by adding a flow and position sensitive coupling into the piston rod, similarly principled as in earlier descriptions. This arrangement can be very advantageous in a skiing knee joint wherein free slow movement is required. However, when control is lost, the knee can stiffen up at a predetermined knee angle, according to location of (x)—per accompanying graph FIG. 4*ki*, so that according to speed and position, a valve is conditioned by flow.

Referring now to FIG. 4*a*, an example valve 47*a* is shown having an inlet 471*a* set within a movable cap 472*a* having a cylindrical skirt 473*a* which is fitted for resilient movement within a bore defined in a base member 474*a*, which cap is closely fitting within the bore; a spring biasing element 475 urges the cap away from the inside of the base member 474*a*, movement of the cap being delimited by an abutment means (not shown). Cap 472*a* has an aperture 471*a* which provides an opening to a fluid flow path within the base member to exit aperture 476*a*. When an increase in hydraulic pressure exists relative to an exit volume (the accumulator pressure) then the cap is urged against the force of the biasing element and moves inwardly toward the base member, whereby the skirt 473*a* occludes the exit aperture 476*a*.

Figure 4B:
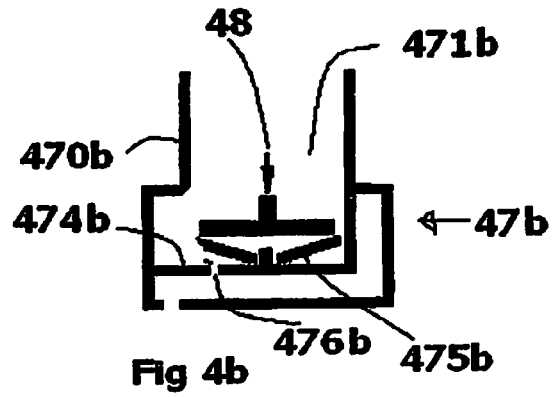

Referring now to FIG. 4*b*, an example valve 47*b* is shown having an inlet 471*b* defined between the lips 470*b* of a base member 474*b*. A movable cap susceptible to pressure control rod 48, for example, comprises a resilient disc spring 475*b*. As will be appreciated in quiescent state, spring biasing element 475*b* urges the cap away from the inside of the base member 474*b*. When an increase in hydraulic pressure exists relative to an exit volume (the accumulator pressure) then the cap is urged against the force of the biasing element and moves inwardly toward the base member, whereby the biasing element retracts toward the base member occluding exit aperture 476*b*.

Figure 4C:
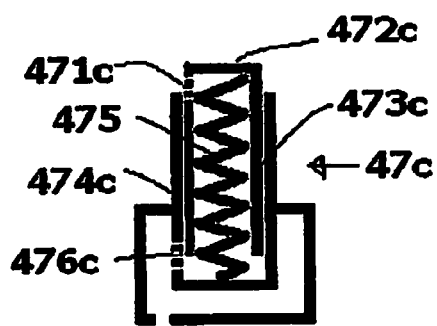

Referring now to FIG. 4*c*, an example valve 47*c* is shown having a movable cap 472*c* having a cylindrical skirt 473*c*. An inlet 471*c* is defined within the skirt 473*c* of the cap. The cap 472*c* is adapted for resilient movement within a bore defined in a base member 474*c*, which cap is closely fitting within the bore; a spring biasing element 475 urges the cap away from the inside of the base member 474*c*, movement of the cap being delimited by an abutment means (not shown). Cap 472*c* has an aperture 471*c* which provides an opening to a fluid flow path within the base member to exit aperture 476*c*. When an increase in hydraulic pressure exists relative to an exit volume (the accumulator pressure) then the cap is urged against the force of the biasing element and moves inwardly toward the base member, whereby to partially occlude the inlet aperture 471*c*; as is the case with FIG. 4*a*, the skirt 473*a* also occludes the exit aperture 476*c*.

Figure 4D:
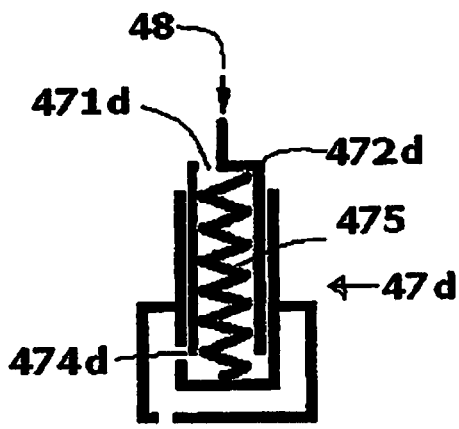

FIG. 4*d* shows a still further variant: valve 47*d* is shown having a movable cap 472*d* having a cylindrical skirt 473*d*. An inlet 471*d* is defined within a closed end of the cap, which is also mechanically connected to the piston 43, pre FIG. 4. The cap 472*d* is adapted for resilient movement within a bore defined in a base member 474*d*, which cap is closely fitting within the bore; a spring biasing element 475 urges the cap away from the inside of the base member 474*d*, movement of the cap being delimited by an abutment means (not shown). Cap 472*d* has an aperture 471*d* which provides an opening to a fluid flow path within the base member to exit aperture 476*d*. When an increase in hydraulic pressure exists relative to an exit volume (the accumulator pressure) then the cap is urged against the force of the biasing element and moves inwardly toward the base member, whereby to partially occlude the exit aperture 476*d*.

Figure 4E:
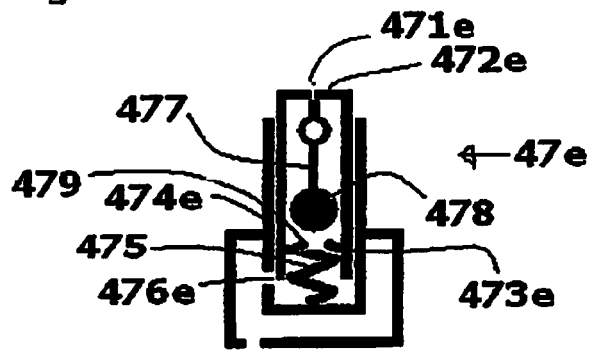

FIG. 4*e* shows a still further variant, although this valve is useful where movement is required when the valve is in a particular orientation in space and may be placed in parallel with another valve or in a parallel fluid circuit. The system includes all the features of valve 47*a*—features of the cap 474*a* & 474*e* correspond, as do the base members 474*a* & 474*e*, skirts 473*a* & 473*e* and exit apertures 476*a* & 476*e*. However pendulum element 477, equipped with a sealing weight member 478, is operable to move when displaced from the vertical and can provide fluid passage with respect to corresponding pendulum valve seat face 479 when not in a vertical orientation. It will be appreciated that a number of these valves can be utilized in groups or on their own. The biasing element can be changed to provide different levels of resilience. Equally, the resilient element is ideally placed upon an adjustable seat member with the base, whereby to enable adjustment, either on build, or conveniently for fine adjustments, once the damper has been fitted within a prosthetic device and an amputee is utilising the device.

With reference to FIG. 4*f*, a hydraulic damper is shown, the valve comprising a vortex inducing chamber 47*f*, also shown in detail. The fluid from the variable volume chamber is guided towards a tangential vortex entrance 471*f* of a circular guide arrangement 480*f* which causes the fluid to rotate about and towards a centrally located exit aperture 476*f* and subsequently pass therethrough. The circular guide need not be exactly circular nor need the aperture be exactly central; differences will affect the operating characteristics, which may be preferred not to be ideal, dependent upon the forces used, the viscosity of the fluid, temperature and other factors. The primary factors of adjustment of the vortex chamber 47*f* are: inlet aperture, radius and height of the chamber and exit aperture. It has been found particularly advantageous if the diameter of the generally circular volume is at least twice the diameter of the outlet aperture.

Reference is now made to FIG. 4*g* which shows a vortex valve in perspective, where the tangential entrance 481 is shown with an arrow leading therefrom with possible paths 482, 483 for fluid to take, dependent upon the relative speed of flow, differential pressure across the valve, relative size of actual inlet and actual exit 476*f* apertures and FIGS. 4*ha*, *b*, *c* & *d* which show a highly developed vortex in an irrotational flow with negligible viscous loss (a), and moving from (b) to (c) to (d) wherein the viscous loss is substantial.

Figure 4I:
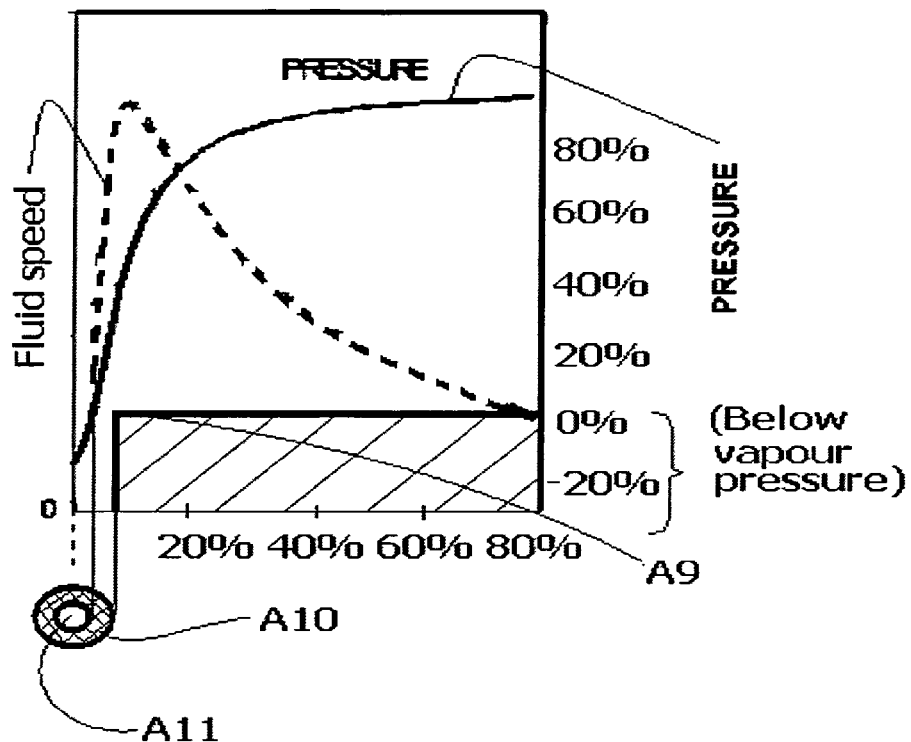

With reference to FIG. 4*i*, the pressure of the hydraulic fluid is shown as a percentage of pressure with respect to a percentage radial distance from the centre of the vortex chamber. Below the x-axis of the graph, an exemplary vortex valve is indicated to provide general correspondence of the vortex itself with reference to operational conditions. A void A11 is indicated where the pressure is below vapour pressure A9, leaving only sectional area A10 of aperture A9 available to fluid flow. As can be seen, as the fluid speed approaches a maximum about the peripheral edge of the exit aperture (akin to a plughole vortex as a bath is emptied) the pressure in the core is reduced and the centrifugal forces empty fluid from the core of the vortex. Thus, a valve with no moving parts is formed and can, surprisingly, provide an effective variable aperture to fluid flow.

Figure 4J:
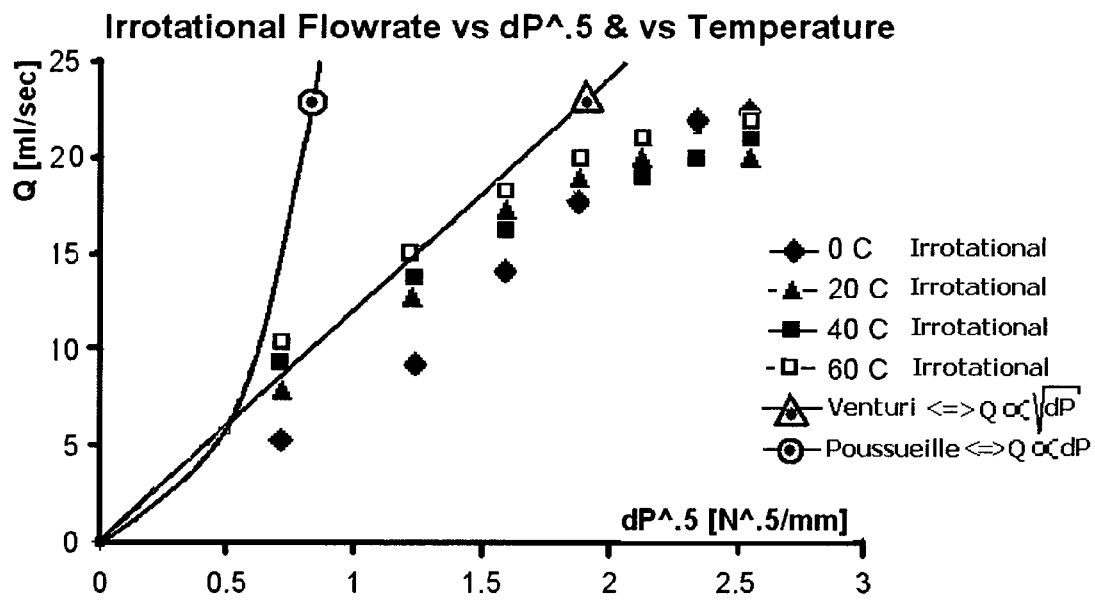

FIG. 4*j* shows a comparison of flow-rates versus change in pressure for irrotational valves in accordance with one aspect of the invention relative to ideal Venturi and Poiseuille plots under the same operating conditions. This shows that with an increase in temperature to a similar asymptotic limit is achieved irrespective of temperature and pressure within a normal set of operating conditions for prosthetics. This has advantage in the temperature stability of use for patients who may travel to hot climates etc. and overcomes a considerable disadvantage of presently known mechanical and hydraulic systems. The graph 4*j* shows the data of a study into the flow characteristics of a 3.5 mm diameter irrotational flow, with a 1 mm$^2$ entry orifice and a 1 mm$^2$ exit orifice. The graph 4*j* shows the relationship between the measured flow and the square root of the pressure, which for a true Venturi flow should deliver a linear relationship, and for any flow that is representative for a condition between Poussuille flow (laminar duct flow) and Venturi (turbulent orifice flow), any trend should be an upward bend of the graph or a steady progression. and not a downward trend as the data show. Further the independence to temperature is well illustrated.

Accordingly, in one aspect of the invention, there is provided a pressure sensitive valve wherein inlet fluid is caused to circulate about a central aperture. Upon attainment of an appropriate flow rate through the vortex valve, a void is induced. The creation of a void, which is believed to comprise hydraulic oil vapours, effectively reduces the aperture dimensions, thus restricting flow. In turn, the flow of fluid from the variable volume chamber is reduced, with the result that movement of the piston within the bore is reduced and so any movement is effectively "damped". It will be appreciated that this valve can have many applications associated with fluid control of prosthetics, not just the specific application with which reference has made. It will be appreciated to those skilled in the art that this type of fluid control can be used in ankle joints and other types of joints in sensory control.

Figure 5E:
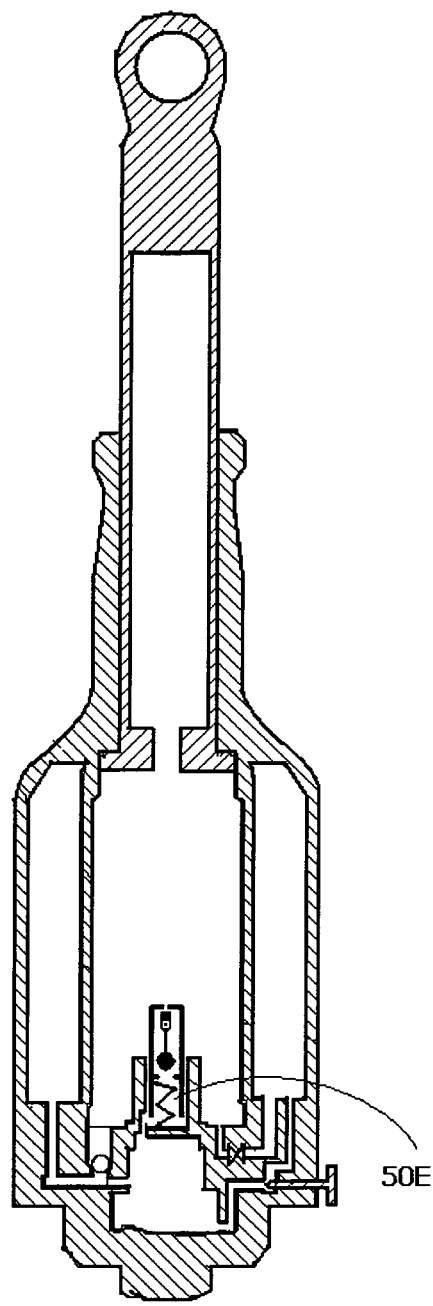

Referring now to FIGS. 5a-5e, there is shown a number of variants, which will be selected to provide a suitable response and operating characteristic for particular patients, amputees etc. FIG. 5a shows in situ a simple embodiment of the valve with a simple metering aperture 50a and the resilient spring has a constant spring rate in its duty range corresponding to the valve described in with reference to FIG. 4a. This can be utilised in a hip joint or ankle joint where uniformity of response is required. A response curve $5bi$ is shown.

FIG. 5b shows a further embodiment wherein the valve mechanism comprises a resilient disc, which covers a correspondingly dimensioned aperture. Since the disc, in operation, closes over the value, the flow, in the limit will be laminar, serving to provide a smooth response. FIG. 5b is an embodiment provided with a gravity sensitive variable metering aperture 50b and shows a valve corresponding to the valve described in with reference to FIG. 4b. A lower build height can also be achieved, which is of particular advantage in small joint prostheses, such as ankles and in prostheses for children.

FIG. 5c is appropriate for geriatric knee joints where, as a leg is lifted off the ground, and only then is swung rearwardly, the inertia of the foot assembly is typically insufficient to cause a complete closure of the valve 47 and the stepped horizontal curve is followed if the patient attempts to collapse on the knee joint whilst: the weight of the patient is sufficient to cause an increase in pressure to cause final closure of the metering aperture 50c. This valve corresponds to fitment of valve 4c. A response curve $5ci$ is shown.

FIG. 5d shows a still further embodiment, wherein the force applied to the valve is conditional upon the extent of insertion of the piston within the bore as well as the force being applied to the hydraulic arm 37. This is enabled by the use of tube, within which the pressure sensing head associated with the pressure feedback device can move; by use of various holes $50d1$, a change in response pressure with respect to piston travel can be enabled. The holes can vary in shape i.e. become narrower toward the coupling end of the hydraulic arm, or vice versa. A response curve $5di$ is shown. FIG. 5e shows in situ a simple embodiment of the valve with a simple metering aperture 50e and the resilient spring has a constant spring rate in its duty range corresponding to the valve described in with reference to FIG. 4e.

The present invention can thus easily and simply have pre-determined response curves which vary in either force or piston distance (or both). A response curve can be created to provide a correct kinematic response tailored for a particular patient.

Referring now to FIG. 6a, there is shown a slide track of knee angle for an amputee wearing a prior prosthetic device. The data, obtained from a You Tube clip, shows the performance of a unilateral transfemoral amputee equipped with a device in accordance with the invention and a comparable device from Ottobock (model 3R80) walking downstairs having a descent angle of 20°. FIG. 6b shows a corresponding comparative test utilising a device in accordance with the present invention. The data form both slide tracks was then entered into a time versus knee angle plot and a time versus knee flexion rate. As shown in FIGS. 6c and 6d, respectively. The first graph should take the 0.2-0.5 seconds time period to be of most relevance, since the earlier times cannot be taken into account in view of the fact that the heel of the other foot must be taking some weight and so the weight would not be born only by the prosthetic device; the latter period cannot be taken into account since the toe of the other foot would be touching and so the weight would not be born only by the prosthetic device. It can be seen that the knee angle of the device in accordance with the invention as plotted is extremely straight indicating that the knee flexion rate in degrees per unit time is effectively constant as is borne out in the graph of FIG. 6d. It can be seen that the variation in knee flexion rate of the prior device is constantly varying, which cannot assist an amputee or wearer of a support brace with a similar extension/flexion function.

In the use of a device in accordance with the present invention a constant rate of knee flexion is indicated, due in part to the pressure compensated flow control: the knee angle reaches a peak and becomes reasonably constant, indicating the joint flexion rate is stabilized. In contrast, in the use of a 3R80 joint, there is shown a rapid acceleration in knee flexion angle. The acceleration exhibited by the prior device represents an extra variable in the already difficult situation in down slope and downstairs descent for the amputee to take into account in planning coordinated movement. Furthermore, it is to be noted that the above data is obtained from uniformly descending surfaces; it will be appreciated that in the event the descent is irregular, for example in country parks etc., then ease and predictability in descent is vital for safety and comfort.

FIG. 7 is a graph that represents the maximum knee flexion angle in swing at various walking speeds for an amputee walking with the aid of the present invention. The graph shows a minimal change in angular variation of knee flexion movement with respect to an increase in walking speed. The plot of knee flexion for a normal gait, i.e. for a person with the full use of their own limbs is shown for comparative purposes. It can be seen that the variation in knee flexion angle is more or less absent, for both the amputee and a control person, with full use of their own legs, despite an increase in speed to approximately double that of the initial speed. In simple terms, to the casual observer, the person wearing such artificial limbs would be seen to have an ungainly gait due to a delay in knee extension needed to prepare the limb for weight acceptance.

Problems arising from the use of weight activated knee joint control mechanisms include the fact that the residual weight taken by the artificial limb on toe off can interfere with the walk and the knee flexion range is adjusted to 65°-70°, as opposed to a natural knee flexion range of 55°-60°. The knee flexion range can be adjusted to correspond closely with the knee flexion range of a natural leg, but this has been found not to be as beneficial as with the case of a slight increase. It is to taken into account that the prosthetic leg and foot cannot provide feedback signals to the user of the leg relating to proximity to the ground and other objects upon or close to the ground and it has been found that the simple expedient of ensuring a slightly greater range of knee flexion reduces a risk of grounding the foot in normal use.

FIG. 8 shows a hip joint in side elevation. It will be appreciated that the hydraulic damper 35 can be utilised in hip replacement situations: an upper limb member 71 is attached to a hip base 70 at hip termination element 72 by connection and pivot point 74. Hydraulic damper is connected at point 76 and 74. Whilst outwardly similar, the internal functions are reversed, since the operational modes of the upper limb is opposite to that of the lower limb, However, this sort of issue can easily be attended to by a reversal of relevant functional features within the damper. It will be appreciated that the hydraulic damper configuration, is suitable for other orthopaedic prostheses.

The anterior placement of the joint centre hip joint in a prosthesis is typically a monocentric or polycentric structure, and is typically placed with a centre of rotation or centres of instantaneous rotation anterior to the natural hip position in relationship to the human body wearing the prosthesis. This relationship is unique in that the axis of operation is significantly more offset in an anterior way, relative to the anatomical joint centre, more than in any other prosthetic joint. The anterior placement causes special problems to occur, problems not seen in the use of other prosthetic joints, and hence have a problem unique to this subclass of prosthetic joints.

This has several consequences. When a free hip is used, the hip and limb need to be swung forward for any next step to be taken. When the foot touches the ground and weight is accepted, the weight acceptance enters in the patient-prosthetic-socket-assembly anterior to the patient's weight line, and this causes a momentum about the pelvis, causing lumber flexion in the spine. This typically continues until the socket finds a secondary support in the hip joint, such as a mechanical stop, allowing a lumbar flexion substantially equal to the hip flexion that was produced to make the forward stride in the first place. This is proprioceptively complex, kinematically difficult, and potentially uncomfortable in terms of the socket-body interaction.

The present invention provides that the positions of the hydraulic parts in walking and in sitting can be distinguished and full hip flexion as in sitting can switch on a memory function allowing effortless standing up, which for the purposes of comparison, and relative to the joint device itself, is equivalent to the swing phase in the knee. As soon as a hip flexion follows, as in walking, the hip flexion disables the memory, and the hip returns to a high resistance mode to hip extension. Known simple hip extension hydraulic apparatus for non-resisting hip flexion systems can be fine for walking, but problems occur not only in sitting but also in the transitions from sitting to standing and from standing to sitting.

Apart from the dynamic control provided by the hydraulics, the axial alignment of the joints can be of significance to good dynamic interaction between prosthesis and body.

The present invention enables the movement control operating mechanism effectively independent of the pivot mechanism. That is to say, many pivot mechanisms such as knee designs can be mono centric, where there is a single pivot of the gross motion of the artificial limb, whilst there are also several designs are so called polycentric, where a number of linkages cooperate to provide a complex gross motion. Whether the total motion of the knee joint is complex or simple, the stability still needs to be assured, and any swing phase needs to be controlled and a damper in accordance with the present invention can provide significant benefit.

Electronic devices need to take fluidic information, use sensors that make electronic signals, these need to be digitised, modified and controlled by fixed or variable data processing modules, and the output thereof needs to be fed to electromechanical or electromagnetic actuators that act as a fluidic control. The energy for this process is typically electrical, most often from rechargeable energy packs. The use of depleting energy supply forms a tie to the user, who needs to recharge these regularly, which can be difficult in travel.

Even though polycentric knees have name to be inherently stable, some of the more inherently stable polycentric designs are actually inherently very unstable if the target of near complete knee extension prior to heel strike is not met. In any of these knee joints it is possible to find or create suitable connection points of relative motion, that if their mutual distance were controlled, an enhancement of total limb control would be achieved.

It is of note that artificial limbs may be fitted below the knee, more typically at or just above the knee, although there is still a significant number of amputees with no remaining bones in a leg. This obviously has significant implications in practice. For example, the product is less likely to be of value in deployment in third world countries, for example, especially those countries have been war-torn over the years. Land mines and other anti-personnel devices are still being found, despite the passage of many years after the cessation of hostilities.

The graph shows the data of a study into the flow characteristics of a 3.5 mm diameter irrotational flow, with a 1 $mm^2$ entry orifice and a 1 $mm^2$ exit orifice.

The diagram shows the relationship between the measured flow and the square root of the pressure, which for a true Venturi flow should deliver a linear relationship, and for any flow that is representative for a condition between Poussuille flow (laminar duct flow) and Venturi (turbulent orifice flow), any trend should be an upward bend of the graph or a steady progression, and not a downward trend as the data show. Further the independence to temperature is well illustrated.

The invention claimed is:

1. A prosthesis comprising:
a first artificial limb component;
a second artificial limb component;
a joint pivotally coupling said first and second artificial limb components to permit extension and flexion movements about the joint; and
a hydraulic damper comprising a variable volume chamber for hydraulic fluid coupled between said first and second limb components;
wherein the damper is operable to allow relative movement of said first and second limb components about the joint by passage of an incompressible hydraulic fluid through said variable volume chamber via an aperture of a valve, the valve being operable to determine a degree to which the hydraulic damper reactively resists a force to permit movement by a first pressure, which first pressure acts on a wall of the variable volume chamber;
wherein the valve is disposed between the variable volume chamber and a hydraulic fluid sink on a second side of the valve;
wherein a fluid flow rate of the incompressible hydraulic fluid through the valve is a conditioned function of a second pressure, which second pressure is less than the first pressure and is associated with fluid flow through the valve and is operable to maintain a positive flow rate through the valve as the first pressure increases, the conditioned function being characterized in that the second pressure as a function of the flow rate causes an increase in resistance of the valve to the flow caused by the first pressure, such that the fluid flow approaches but does not reach a maximum as the first pressure increases past a minimum pressure, whereby a fluid flow limit is established through the valve.

2. The prosthesis of claim 1, wherein the second pressure acts upon a moveable element against a resistance provided by a resilient element to vary the fluid flow rate.

3. The prosthesis of claim 2, wherein the second pressure is further conditioned by one or both of a position of the moveable element and a position of a gravity sensitive element or by a relative position of the first and second artificial limb components.

4. The prosthesis of claim 2, wherein the moveable element comprises the resilient element and wherein the second pressure is derived from a flow through an inlet aperture remote to the outlet aperture acting on a surface of the resilient element occluding the aperture according to a relative proximity of the resilient element to the aperture and a resilience of the resilient element.

5. The prosthesis of claim 2, wherein there is an outlet aperture of the valve defined in a wall of a base of the valve and the moveable element moves in a direction towards the base whereby to occlude the aperture, at least in part, wherein the width of the aperture varies in the direction of movement, whereby to allow a nonlinear change in output flow with respect to movement of the moveable element.

6. The prosthesis of claim 2, wherein there is an outlet aperture of the valve defined in a wall of a base of the valve and the moveable element moves in a direction towards the base whereby to occlude the aperture, at least in part, wherein the effective size of the aperture varies in stepwise fashion in the direction of movement, whereby to allow a stepped change in output flow with respect to movement of the moveable element.

7. The prosthesis of claim 2, wherein there is an outlet of the valve defined in a wall of a base of the valve, the outlet comprising a plurality of outlet apertures, and the moveable element moves in a direction towards and across the outlet apertures whereby to occlude the outlet apertures, at least in part, whereby to provide a nonlinear change in output flow with respect to movement of the moveable element.

8. The prosthesis of claim 2, wherein there is an inlet of the valve defined in a wall of the moveable element of the valve, the inlet comprising a plurality of inlet apertures, and the moveable element moves in a direction with respect to a wall of a base of the valve whereby to occlude one or all of the plurality of inlet apertures, at least in part, whereby to provide a change in output flow with respect to movement of the moveable element.

9. The prosthesis of claim 2, wherein the resilient element comprises a disc spring mounted with respect to a base of the valve and wherein an aperture of the valve lies on the base of the valve and wherein the aperture can be occluded, at least in part, by the disc spring when the disc spring is subject to a force arising from resistance to flow through an aperture associated with fluid flow through the valve.

10. The prosthesis of claim 2, wherein the second pressure is further determined by a relative position of a gravity sensitive element with respect to the valve.

11. The prosthesis of claim 2, wherein the variable volume chamber is defined by a hydraulic actuator comprising a piston operable within a bore having a closed end and equipped with a valve, the variable volume being defined between the piston and the closed end of the bore.

12. The prosthesis of claim 1, wherein the second pressure acts upon a moveable element against a resistance provided by a resilient element to vary the fluid flow rate, wherein the force created to overcome the resistance is further conditioned by a relative state of the hydraulic damper and the degree of extension/flexion of the limb elements.

13. The prosthesis of claim 1, wherein the second pressure acts upon a moveable element against a resistance provided by a resilient element to vary the fluid flow rate and wherein the second pressure is determined by the flow through an inlet aperture.

14. The prosthesis of claim 1, wherein the second pressure acting upon a moveable element against a resistance provided by a resilient element to vary the fluid flow rate, wherein the second pressure is further conditioned by a relative state of the hydraulic damper and a degree of extension/flexion of the limb elements, wherein the second pressure is determined by the flow through an inlet aperture.

15. The prosthesis of claim 1, wherein the variable volume chamber is defined by a hydraulic actuator comprising a piston operable within a bore having a closed end and equipped with the valve, the variable volume being defined between the piston and the closed end of the bore.

16. A prosthesis comprising:
a first artificial limb component;
a second artificial limb component;
a joint pivotally coupling said first and second artificial limb components to permit extension and flexion movements about the joint; and
a hydraulic damper comprising a variable volume chamber for hydraulic fluid coupled between said first and second limb components;
wherein the damper is operable to allow relative movement of said first and second limb components about the joint by passage of an incompressible hydraulic fluid through said variable volume chamber via an aperture of a valve, the valve being operable to determine a degree to which the hydraulic damper reactively resists a force to permit movement by a first pressure, which first pressure acts on a wall of the variable volume chamber;
wherein the valve is disposed between the variable volume chamber and a hydraulic fluid sink on a second side of the valve;
wherein a fluid flow rate of the incompressible hydraulic fluid through the valve is a conditioned function of a second pressure, which second pressure is less than the first pressure and is associated with fluid flow through the valve operable to maintain a positive flow rate through the valve as the first pressure increases, the conditioned function being characterized in that the second pressure as a function of the flow rate causes an increase in resistance of the valve to the flow caused by the first pressure, such that the fluid flow approaches a maximum as the first pressure increases past a minimum pressure, and on further increase of the first pressure the fluid flow approaches a maximum and remains unchanged as the first pressure increases beyond the minimum pressure, whereby a fluid flow limit is established through the valve;
wherein the valve is a vortex chamber and wherein the second pressure is a function of a tangential speed of a fluid flow within the vortex chamber such that at critical speeds of fluid flow a void is formed within the vortex chamber, thereby maximizing the second pressure to oppose the first pressure.

17. The prosthesis of claim 16, wherein the second pressure is determined by an effective aperture size of at least one of an inlet aperture and an outlet aperture of the valve.

18. The prosthesis of claim 16, wherein the variable volume chamber is defined by a hydraulic actuator comprising a piston operable within a bore having a closed end and equipped with the valve, the variable volume being defined between the piston and the closed end of the bore.

\* \* \* \* \*